United States Patent [19]

Kalopissis et al.

[11] 4,001,141
[45] Jan. 4, 1977

[54] COSMETIC EMULSIFIERS

[75] Inventors: Gregoire Kalopissis, Paris; Guy Vanlerberghe, Montjay-la-Tour, both of France

[73] Assignee: L'Oreal, Paris, France

[22] Filed: June 6, 1975

[21] Appl. No.: 584,499

Related U.S. Application Data

[60] Division of Ser. No. 480,671, June 17, 1974, Pat. No. 3,914,407, which is a division of Ser. No. 119,363, Feb. 26, 1971, Pat. No. 3,824,294, which is a continuation-in-part of Ser. No. 780,299, Nov. 29, 1968, abandoned, which is a continuation-in-part of Ser. No. 677,047, Oct. 23, 1967, Pat. No. 3,595,924.

[30] Foreign Application Priority Data

Oct. 21, 1966  Luxembourg ............... 52227
Oct. 24, 1966  Luxembourg ............... 52228
Oct. 6, 1967   Luxembourg ............... 54622
Dec. 1, 1967   France ............... 67.130712

[52] U.S. Cl. .................. 252/351; 8/10.1; 106/308 F; 106/308 Q; 252/309; 252/312; 252/316; 252/DIG. 1; 260/611 A; 260/611 B; 424/64; 424/69; 424/170; 424/358

[51] Int. Cl.$^2$ ......................... B01F 17/42

[58] Field of Search .............. 252/351, 309, DIG. 1

[56] References Cited

UNITED STATES PATENTS

| | | | |
|---|---|---|---|
| 3,102,893 | 9/1963 | Gaertner | 252/DIG. 1 |
| 3,578,719 | 5/1971 | Kalopissis et al. | 252/351 X |
| 3,594,409 | 7/1971 | Lachampt et al. | 424/365 X |
| 3,666,671 | 5/1972 | Kalopissis et al. | 252/351 X |
| 3,846,546 | 11/1974 | Lachampt et al. | 252/351 X |

*Primary Examiner*—Richard D. Lovering
*Attorney, Agent, or Firm*—Cushman, Darby & Cushman

[57] ABSTRACT

An emulsifying and peptizing agent having the formula

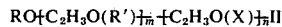

wherein
R is a lipophilic hydrocarbon residue of a member selected from the group consisting of alcohols, sterols and their mixtures derived from a member selected from the group consisting of (a) hydrogenated lanolin, and (b) cyclic fatty acids,
R' is selected from the group consisting of methyl and ethyl,
X is selected from the group consisting of —CH$_2$OH,

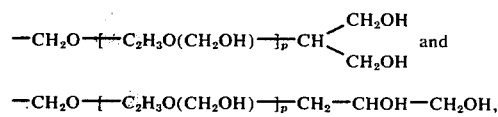

—CH$_2$O$\overline{\phantom{x}}$C$_2$H$_3$O(CH$_2$OH)$\overline{\phantom{x}}$$_p$—CH$_2$—CHOH—CH$_2$OH, $m$ has a statistical average value between 1–10 inclusive,
$n$ has a statistical average value between 1–5 inclusive,
$p$ is an integer between 0–10 inclusive and the product $n(p+2)$ lies between 2–12 inclusive.

1 Claim, No Drawings

COSMETIC EMULSIFIERS

This application is a division of application Ser. No. 480,671, filed June 17, 1974, now U.S. Pat. No. 3,914,407, which is a division of Ser. No. 119,363, filed Feb. 26, 1971, now U.S. Pat. No. 3,824,294, which is a continuation-in-part of Ser. No. 780,299, filed Nov. 29, 1968, now abandoned, which is a continuation-in-part of Ser. No. 677,047, filed Oct. 23, 1967, now U.S. Pat. No. 3,595,924.

The present invention relates to chemical compounds usefully employed as cosmetic emulsifiers or peptizers. These compounds are non-toxic and do not become rancid. The present invention is also related to a method for preparing these new chemical compounds.

In accordance with the present invention, there is provided a chemical compound having the formula $$RO[C_2H_3O(R')]_m[C_2H_3O(X)]_n H \qquad (I)$$

wherein

R is a lipophilic hydrocarbon residue of a member selected from the group consisting of alcohols sterols or their mixtures derived from a member selected from the group consisting of (a) hydrogenated lanolin, and (b) cyclic fatty acids, R' is selected from the group consisting of methyl and ethyl, X is selected from the group consisting of $-CH_2OH$, $$-CH_2O-[-C_2H_3O(CH_2OH)-]_p-CH\begin{smallmatrix}CH_2OH\\ \\CH_2OH\end{smallmatrix} \text{ and}$$

$$-CH_2O-[-C_2H_3O(CH_2OH)-]_p-CH_2-CHOH-CH_2OH,$$

$m$ has a statistical average value of between 1–10 inclusive, preferably between 2–6 inclusive, $n$ has a statistical average value between 1–5 inclusive, $p$ is an integer between 0–10 inclusive and the product $n(p + 2)$ lies between 2–12, inclusive.

The method of the present invention for producing these novel compounds comprises the steps of (1) polycondensing on a compound having the formula ROH wherein R has the meaning given above an epoxide having the formula $$R'-\underset{\underset{O}{\diagdown\diagup}}{CH-CH_2}$$

wherein R' has the meaning given above and thereafter a halogen containing member having the formula $$Y-\underset{\underset{O}{\diagdown\diagup}}{CH-CH_2}$$

wherein Y is selected from the group consisting of $-CH_2Z$, $$-CH_2O-[-C_2H_3O(CH_2Z)-]_p-CH\begin{smallmatrix}CH_2Z\\ \\CH_2Z\end{smallmatrix} \text{ and}$$

$$-CH_2O-[-C_2H_3O(CH_2Z)-]_p-CH_2-CHZ-CH_2Z$$

wherein Z is selected from the group consisting of chlorine and bromine, at a temperature between 25°–150° C in the presence of an acid catalyst selected from the group consisting of boron fluoride, antimony pentachloride and stannic chloride, (2) hydroxylating the resulting condensate from (1) by esterifying with alkaline acetate at a temperature between 150°–200° C in the presence of a solvent selected from the group consisting of propylene glycol, dipropylene glycol, diethylene glycol, the ethers of diethylene glycol, ethylene glycol, hexylene glycol and 2-butoxy ethanol, said alkaline acetate being present in amounts ranging between stoichiometric and 15% in excess of stoichiometry based on said halogen containing member and said solvent being present in amounts of at least 50% of said halogen-containing member and (3) deacylating by alcoholysis the ester formed in (2) above.

One object of the present invention is to enlarge the class of non-ionic surface active agents described in our aforementioned earlier applications by adding thereto those which can be prepared from natural or synthetic aliphatic or alicyclic alcohols and/or sterols having a high molecular weight. By natural alcohols and sterols are meant those derived, for example, from hydrogenated lanolin, and from reduced cyclic fatty acids.

It is known, for instance, that the lanolin alcohols comprise up to 30 carbon atoms and that they consist of a mixture of the aliphatic series having straight or branched chains (iso and anteiso derivatives) and alcohols of the alicyclic series (sterols and triterpenic alcohols). The alcohols are found in lanolin, essentially in the form of esters of fatty acids. Hydrogenation yields a mixture containing both alcohols from the unsaponifiable constitutents and those from the fatty acids of lanolin.

The preparation of lanolin alcohols by hydrogenation was described by Stockdorn, E. Konig and Birk in the Tenside review, 3, No. 2 (1966) p.45.

"Elrolan" sold by VEB Deutsches Hydrierwerk and "Hydrolan R" sold by Occo International, Division of Millmaster Onyx Corporation, Jersey City, N.J. U.S.A are examples of alcohols of lanolin prepared by hydrogenation.

Representative cyclic fatty alcohols derived from cyclic fatty acids include those of the following formulae wherein $x + y = 10$ and wherein $x + y = 12$.

The non-ionic surface active agents envisaged by the present application can be employed in emulsions containing as an emulsifier a compound having formula (I) and especially in cosmetic products, for example in hydrating creams or nourishing creams, or in pharmaceutical excipients. They can also be used as carriers for hair dyes. For example, hair dyes sold in gel form, containing a compound having formula (I). Addtionally, the compounds of this invention can be used to produce dispersions of solid pulverulent products in liquid media and especially in oils. The novel compounds of this invention are employed as peptizing agents to produce such dispersions.

The compounds having the above formula (I) are, in general, emulsifiers which make it possible to form "water-in-oil" emulsions, especially when the product $n(p+2)$ is less than about 4. In such emulsion, water is present in amounts of about 20 to 70 weight percent, oil in amounts of about 25 to 70 weight percent and the emulsifiers in amounts of about 5 to 25 weight percent.

When the product $n(p+2)$ is greater than about 4, the compounds of formula (I) are generally employed as emulsifiers to produce "oil-in-water" emulsions. These emulsions comprise about 30 to 65 weight percent water, 30 to 60 weight percent oil and 10 to 25 weight percent of said emulsifier.

It should be noted that, in a given compound, the R' radicals which are substituents on the ethoxamer can be identical or different. In the latter case, they may be distributed in various proportions, either in regular sequences or in an irregular manner, depending on whether the pure epoxides are poly added in several distinct steps or mixtures of propylene oxide and butylene oxide are used.

In a preferred embodiment of the present invention, polycondensation is carried out in an autoclave or in a container connected to the ambient atmosphere through a reflux condenser. When the polycondensation catalyst is boron fluoride, this is used in the form of a complex with acetic acid or ether. The quantity of boron fluoride in terms of $BF_3$ per 100g of reactants, is between 0.1 and 1%, and preferably about 0.4–0.5%. The temperature should preferably be kept below 100° C, for example 70° and 80° C.

The hydroxylation which constitutes the second step of the process is based on the reaction of the halogen derivative obtained in the first step with an alkaline salt of carboxylic acid, preferably in a solvent bath which insures both the miscibility of the reactants and the easy separation of the mineral halide formed. In this method, the selected solvents participate through progressive alcoholysis of the esters formed in an intermediate stage. Among the solvents having the required properties are propylene glycol, dipropylene glycol, diethylene glycol, the ethers of diethylene glycol, ethylene glycol, hexylene glycol, and 2-butoxy ethanol, the boiling points of which are high enough to make the use of an autoclave unnecessary. In general, it has been found that the quantity of solvent to be used during hydroxylation should be at least 50% as much by weight as the polyhalogenated ether which is to be hydroxylated, and preferably between 100 and 400% as much. The hydroxylation is carried out at a temperature high enough to complete the reaction within a reasonable length of time, and low enough to avoid degradation of the products formed. A temperature between 150° and 200° C, and preferably between 180° and 190° C satisfies these conditions. About 90% hydroxylation results.

The alkaline salt of carboxylic acid used in the process may advantageously be an alkaline acetate such as potassium acetate, sodium acetate and the like employed in a stoichiometric proportion, or in slight excess (10 to 15% at most) with respect to the halogenated compounds participating in the reaction. It has been found that the results are equally satisfactory regardless of whether the acetates are added all at once at the beginning of the hydroxylation step, or in successive stages during the course of this reaction. It is possible to regenerate the acetates in situ from the esters formed during the reaction, for example, by adding an aqueous solution of a corresponding alkaline hydroxide and instantaneously evaporating the water.

In order to avoid coloring the products obtained during hydroxylation reducing agents such as sodium hypophosphite or alkaline borohydrides may be added.

The crude products obtained by this process may advantageously be purified by washing them in hot water. The water soluble impurities, and particularly the electrolytes are thus eliminated and this is particularly desirable when the water-in-oil type of emulsion is prepared.

When the products of formula (I) are to be used in emulsions of the water-in-oil type, the preferred products are those having a relatively short hydrophile chain in which $n$ has, for example, a value between 2 and 3 and X represents hydroxymethyl.

When the products of formula (I) are to be used in emulsions of the oil-in-water type, the preferred products are those having a relatively long hydrophile chain, in which, for example, $n$ is greater than 3 when X represents hydroxymethyl.

The following "oils" illustrate the kind of oil that could be used in the water-in-oil or in the oil-in-water type of emulsion:
1. hydrocarbons such as paraffin oil, liquid petrolatum, squalane or perhydrosqualane;
2. animal and vegetable oils such as horse grease, lard, lard oil, sweet-almond oil, peanut oil, olive oil, calophyllum;
3. esters such as oleyl oleate, isopropyl myristate, isopropyl palmitate and isopropyl stearate.

When the emulsifiers which are strongly hydrophilic are desired, the value of $n$ should be greater than 1 and, better yet, when X respresents the $CH_2OH$ radical, at least equal to 2. Moreover, the parameter $m$ should have a value high enough so that the oxypropylenated or oxybutylenated alcohol obtained in the first polycondensation step has a melting point below 40° C. The lower limits of $m$ and $n$ are thus determined by the physiochemical properties of the emulsifiers produced.

The non-ionic surface-active agents in this invention can be used as emulsifiers in formulating cosmetic compositions or pharmaceutical excipients, as carriers for hair dyes, or as peptizers in producing dispersions of pulverulent products. They are non-toxic, even when applied to the skin, which is a very important criterion when cosmetic applications are envisaged.

The present invention is also directed to emulsions which can be used, particularly in cosmetic products or in pharmaceutical excipients, essentially characterized by the fact that they contain, as an emulsifier, at least one compound according to formula (I).

In the cosmetic field the compounds according to formula (I) can serve as bases for hydrating milks, cleansing creams, or nourishing creams. They can also be used as carriers for hair dyes, and in that case may produce such dyes in the form of a gel.

Another object of the present invention is therefore to provide a dye composition for human hair essentially characterized by the fact that it comprises as a carrier at least one compound according to formula (I) in amounts of about 10 to 30 weight percent based on dye composition mixed with conventional cosmetic hair dye.

The new chemical compounds according to formula (I) can also act as peptizing agents, which are particularly efficacious in dispersing solid powdered material in liquid media, and especially in oil. Generally the peptizing agent will be present in amounts of about 5 to 15 weight percent of the solid powdered material.

It is therefore another object of the present invention to provide dispersions of solid pulverulent products in liquid media and particularly in oils, characterized by the fact that they contain as peptizing agents at least one compound according to formula (I).

To illustrate the invention, several examples thereof will now be described.

EXAMPLE 1

Preparation of the product represented by the formula:

$$RO[C_2H_3O(CH_3)]_{\overline{n}}[C_2H_3O(CH_2OH)]_{\overline{n}}H$$

in which R represents a hydrocarbon residue derived from a lanolin alcohol obtained by catalytic hydrogenation of lanolin and sold under the trademark ELROLAN by VEB DEUTSCHES HDRIERWERK.

First Step: Polycondensation of propylene oxide and epichlorohydrin 41.3 g of the above-mentioned lanolin alcohol is first melted and vacuum-dried. 0.45 ml of an acetic complex of boron fluoride is then added, followed successively by 17.4 g of propylene oxide and 18.5 of glycerol epichlorohydrin. The temperature of the reaction is 75°–80° C and it lasts 45 minutes.

The product is a clear brown polychlorinated polyether.

Second Step: Hydroxylation 62 g of the chlorinated polyether thus obtained is added to 15.7 g of potassium acetate dissolved in 80 g of dipropylene glycol. The reaction mixture is heated to 180°–185° C for 3 hours and 30 minutes under a nitrogen atmosphere.

After cooling to 70° C, the potassium chloride is separated by filtration and the precipitate washed with 50 g of hot dipropylene glycol. The solvent is evaporated from the filtrate, under a vacuum, while it is being agitated, and while increasing the temperature progressively to 185° C. The crude product obtained in this manner has a saponification index of 22 mg KOH/g. The product is then subjected to ethanolysis by dissolving it in 100 ml of absolute ethyl alcohol and adding sodium methylate as a catalyst at the rate of 0.275 g per 100 g of the product to be treated.

The alcoholic solution is left overnight at ambient temperature and then bleached with animal charcoal. After evaporation of the ethyl acetate and the alcohol, an amber-yellow solid is recovered, the average composition of which is given at the beginning of this example. It can be purified by washing with a hydroalcoholic solution containing 15% ethyl alcohol.

EXAMPLE 2

Fluid Skin Treating Cream

The following composition is prepared:

| | |
|---|---|
| Compound of Example 1 | 9 g |
| Lanolin alcohol sold under the trademark "Super Hartolan" by the Croda Company | 4 g |
| Vaseline | 11.5 g |
| Perhydrosqualene | 10 g |
| Microcrystalline wax | 4.5 g |
| Water, q.s.p. | 100 g |

The scope of the invention is not limited to the foregoing examples, and the examples could be modified as to detail without departing from the basic principles of the invention. In particular the hydrophilic property of the compounds of the invention could be increased by subsequent reaction with one or more molecules of ethylene oxide. Moreover, the compounds according to the invention may be transformed by known processes, into ionic surface-active agents by introducing ionic groups into the compound structure such as sulfonate ions, carboxylate ions, phosphate ions, etc.

Although the examples set forth above use R groups obtained by reacting commercially available fatty alcohol mixtures similar results can be obtained by using a single fatty alcohol or sterol.

The cosmetic compositions according to the present invention may contain, apart from the cosmetics and the compound of formula (I), different adjuvants, for example oil retention ingredients such as lanolin alcohols and microcrystalline waxes.

EXAMPLE 3

This example relates to the peptization of a pulverulent solid, hydrated iron oxide.

Iron oxides are often used in cosmetic compositions but before use they generally have to be washed in order to eliminate impurities. Upon drying they tend to ball together. This re-agglomeration can be avoided by adding in the last washing a surface-active agent having the general formula (I).

The present example relates to iron oxide sold under the trademark "Micron Pink 2511" sold by Thomasset Color.

5% weight of the compound of Example 1 is added in the last washing of the iron oxide. After carefully drying, the resulting powder is perfectly wetted by oils and can be introduced in cosmetic compositions.

Other iron oxides as well as other pigments such as titanium oxides, barium sulfate and Guimet's blue can be peptized in this manner with equally favorable results.

What is claimed is:

1. A composition consisting essentially of a mixture of different compounds, each having the formula $$RO[C_2H_3O(R')]_{\overline{m}}[C_2H_3O(X)]_{\overline{n}}H$$

wherein R is a lipophilic hydrocarbon residue of a member selected from the group consisting of hydrogenated lanolin,

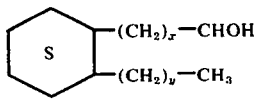

wherein $x + y = 10$ and

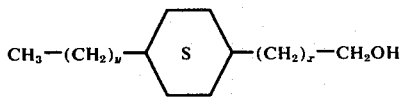

wherein $x + y = 12$, R' is selected from the group consisting of methyl and ethyl, X is selected from the group consising of —CH$_2$OH,

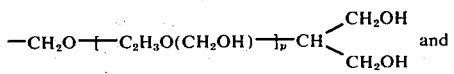

and

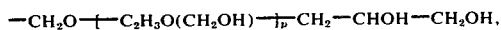

$m$ has a statistical average value between 1–10 inclusive, $n$ has a statistical average value between 1–5 inclusive, $p$ is an integer between 0–10 inclusive and the product $n(p+2)$ lies between 2–12 inclusive, said mixture being present in surface-active amounts in said composition.

* * * * *